United States Patent [19]

Abu-Shumays et al.

[11] 4,181,853

[45] Jan. 1, 1980

[54] LIQUID CHROMATOGRAPHY SYSTEM WITH PACKED FLOW CELL FOR IMPROVED FLUORESCENCE DETECTION

[75] Inventors: Ahmad Abu-Shumays, Los Altos; Edward L. Johnson, Mountain View, both of Calif.

[73] Assignee: Varian Associates, Inc., Palo Alto, Calif.

[21] Appl. No.: 938,738

[22] Filed: Aug. 31, 1978

Related U.S. Application Data

[63] Continuation of Ser. No. 878,976, Feb. 17, 1978, abandoned, which is a continuation of Ser. No. 748,867, Dec. 10, 1976, abandoned.

[51] Int. Cl.² ............................................. G01N 21/34
[52] U.S. Cl. ................... 250/304; 23/232 C; 210/31 C; 250/461 R; 422/69
[58] Field of Search ............... 250/301, 302, 304, 373, 250/461 R; 23/232 C, 254 R; 210/31 C, 198 C; 356/51; 73/23.1

[56] References Cited

U.S. PATENT DOCUMENTS

| 3,200,254 | 8/1965 | Van Luik, Jr. et al. ......... 250/461 R |
| 3,281,596 | 10/1966 | Williston ............................. 250/304 |
| 3,303,043 | 2/1967 | Halpaap et al. ..................... 250/304 |
| 3,581,085 | 5/1971 | Barrett ............................. 250/461 R |
| 3,644,734 | 2/1972 | Inoue et al. ......................... 250/304 |

OTHER PUBLICATIONS

B. L. van Duuren, *Anal. Chem.*, 40:2024 (1968).
J. B. F. Lloyd, *Analyst* (London), 100:529 (1975).
T. Panalaks et al., 90th An. Meeting of the AOAC, Wash. D. C., Oct. 18–21, 1976 (Abstract No. 133).
T. Panalak et al., *Journal of the AOAC*, 60 (3):583 (1977).
B. Zimmerli, *Journal of Chromatography*, 131:458 (1977).

*Primary Examiner*—Davis L. Willis
*Attorney, Agent, or Firm*—Stanley Z. Cole; John J. Morrissey; Gerald M. Fisher

[57] ABSTRACT

In a liquid chromatography system, the effluent from the chromatographic column is passed through a detector flow cell, which is packed with a stationary phase that is adsorptive of the sample species to be detected. Detection of the sample species adsorbed at the stationary phase is effected by measuring fluorescence emitted from such species in response to electromagnetic radiation incident thereon at the flow cell. The fluorescing species, which are in equilibrium between the stationary phase and the mobile phase in the flow cell when fluorescence is being measured, can be detected at lower concentration thresholds than when the fluorescing species are in equilibrium only with the mobile phase.

21 Claims, 4 Drawing Figures

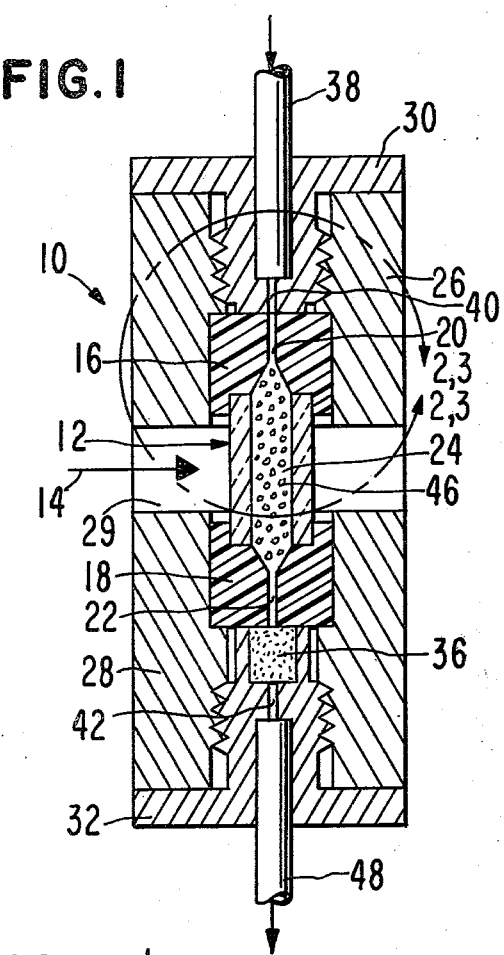
FIG.1
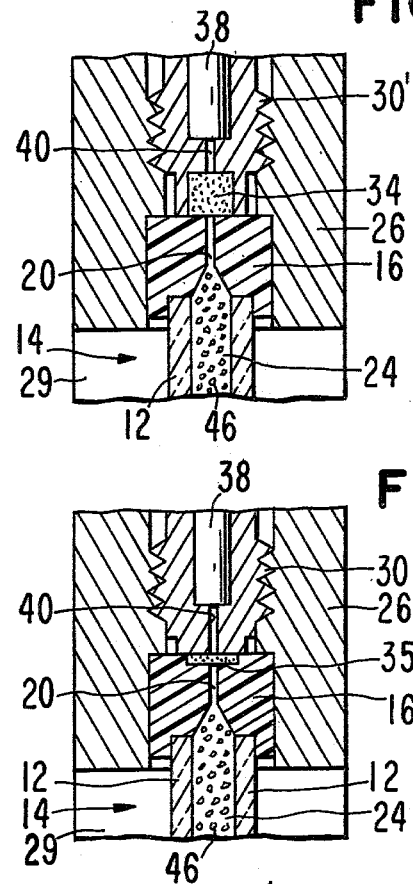
FIG.2
FIG.3
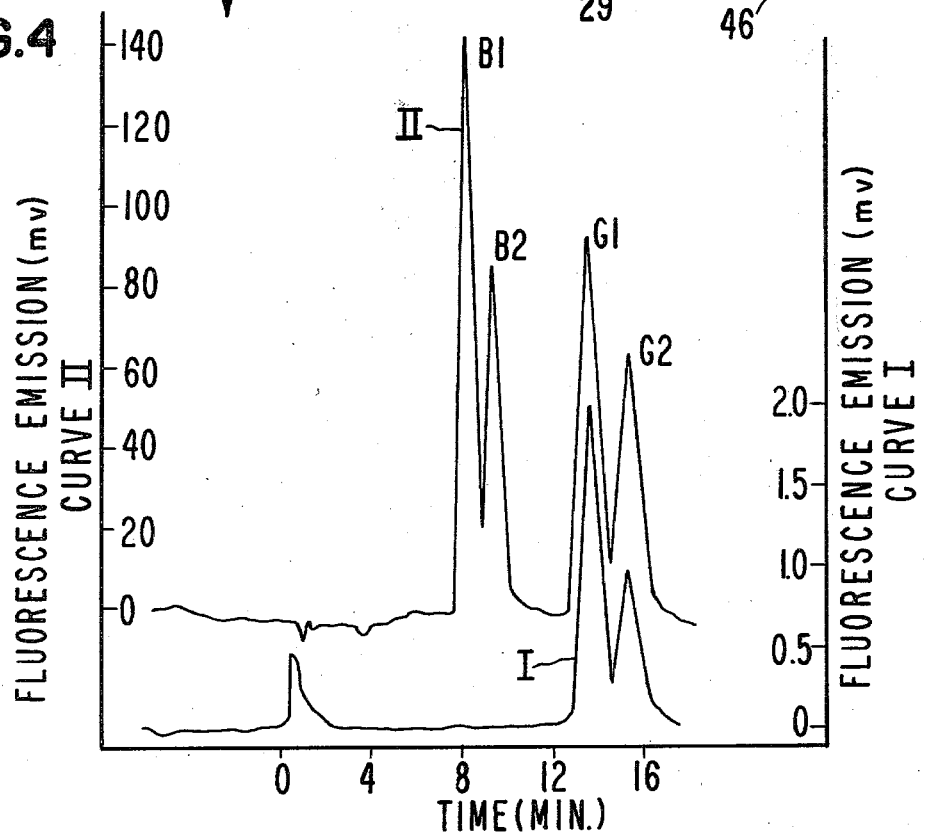
FIG.4

LIQUID CHROMATOGRAPHY SYSTEM WITH PACKED FLOW CELL FOR IMPROVED FLUORESCENCE DETECTION

This is a continuation, of application Ser. No. 878,976 filed Feb. 17, 1978 which is a continuation of Ser. No. 748,867, filed Dec. 10, 1976 both now abandoned.

BACKGROUND OF INVENTION

This invention is a further development in liquid chromatography, and relates specifically to systems that use fluorescence detection for sensing and measuring sample components in the chromatographic column effluent.

Chromatography is a separation technique wherein a mixture of components (called the "sample" or "sample mixture") is placed at one end of a system containing a stationary phase and a mobile phase. Each component of the sample distributes itself as a separate zone within the mobile phase in dynamic equilibrium between the stationary phase and the mobile phase. The mobile phase in flowing through the system causes each individual component zone to migrate at a characteristic rate, and the zones thereby become separated after a period of time.

There are various types of chromatography, e.g., liquid chromatography, gas chromatography, and thin-layer chromatography. The major features distinguishing any one type of chromatography from the other types are the physical state of the mobile phase (e.g., whether gas or liquid) and the manner in which the stationary phase is supported (e.g., whether coated on an inert granular material, packed in a tube, or coated on an inert plate). In each type of chromatography, the separation mechanism is essentially the same, viz, distribution of the sample components between the mobile phase and a stationary phase within a chromatographic column.

When chromatography is used for chemical analysis, a detector is commonly placed at the output end of the column in order to monitor passage of the individual component zones as they emerge from the system. The signal from the detector may be displayed on a recording device such as a strip chart recorder, and the resulting record provides both qualitative and quantitative information regarding the components of the sample.

In liquid chromatography, various kinds of detectors may be used, e.g., detectors measuring the absorption of ultraviolet or visible light, refractive index detectors, and detectors whose operating principles are based upon heat of adsorption, flame ionization, electrical conductivity, or the fluorescence characteristics of the eluting species proceeding from the chromatographic column. In the past, use of the fluorescence detection technique in liquid chromatography has been quite limited, because the fluorescence quantum yield for many compounds of interest is quite low for most commonly used solvents.

In the prior art, the elutant of a chromatographic column was typically passed through a flow cell consisting of a clear channel having radiation-transmissive windows or walls that allow the passage of incident electromagnetic radiation of a preselected wavelength into the flowing elutant. The sample to be detected in the elutant was excited by the incident radiation, and was thereby caused to emit fluorescence that could be detected with a photometric device.

The detection sensitivity for any particular fluorescent compound is dependent on the quantum yield, or quantum efficiency, of the compound and upon the concentration of the compound. The quantum yield is influenced by a number of factors, especially the characteristics of the solvent or mobile phase in which the flourescent compound is carried. Usually, the requirements for chromatographic separation determine the type of solvent used. For many fluorescent compounds carried in nonpolar solvents, which is the technique generally used in normal phase chromatography, the quantum yield is significantly lower than for the same compounds existing apart from such solvents. Thus, in fluorescence detection chromatography a nonpolar mobile liquid phase generally serves to increase the minimum quantity of sample compounds carried therein that can be detected. In some instances, the fluorescence quantum yield for chemical compounds of interest is so low that such compounds simply could not be detected by prior art fluorescence methods. It is generally not advantageous in liquid chromatography to use a solvent that enhances detection sensitivity, because such solvents tend to exhibit other characteristics that significantly compromise the separation resolution of the individual component zones.

SUMMARY OF THE INVENTION

It is an object of this invention to provide method and apparatus to enable improved fluorescence detection of eluting species in the mobile phase proceeding from the column of a liquid chromatography system.

It is a further object of this invention to provide method and apparatus for fluorescence detection in liquid chromatography systems, which function to enhance fluorescence quantum yields for sample component species to be detected and which thereby significantly lower the minimum detectable quantities of such species.

It is likewise an object of this invention to provide method and apparatus that, while enhancing the capability for fluorescence detection of cluting species proceeding from a chromatonraphic column, concomitantly minimize peak broadening effects to avoid significantly altering the separation resolution of the system.

The foregoing objects, and others as will become apparent from a perusal of the ensuing specification, are achieved by passing the elutant from the chromatographic column through a detector flow cell, which is packed with a stationary phase that is adsorptive of the eluting species. Detection of the species thereby adsorbed at the stationary phase may be effected by measuring the fluorescence emitted from such adsorbed species in response to excitation by radiation incident at the flow cell. In consequence of this invention, fluorescing species may be detected at much lower concentration thresholds than have heretofore been detectable.

This invention is particularly applicable in normal phase chromatography, wherein nonpolar solvents are customarily employed. With such solvents, many fluorescent compounds exhibit quantum yields that are significantly lower than when such compounds are irradiated apart from such solvents. In fact, many fluorescent compounds, when in dynamic equilibrium with nonpolar solvents, exhibit such low quantum yields that their minimum detectable concentrations by the fluorescence detection technique are extraordinarily high. Indeed, for some compounds the fluorescence quantum yields in the presence of nonpolar solvents are so low that concentrations of significant interest are undetectable.

In accordance with this invention, a flow cell of the kind customarily used in liquid chromatography is packed with a stationary phase, which may comprise, e.g., silica particles of a few microns average diameter, minute alumina particles, suitable bonded-phase particles, or ion-exchange resins. The stationary phase adsorps the eluting species flowing through the cell. The preferred excitation-emission geometry of the flow cell is characterized by a substantially right angle configuration, i.e., the excitation beam is preferably at 90° relative to the direction at which the emitted fluorescence is observed and measured.

BRIEF DESCRIPTION OF DRAWING

FIG. 1 is a schematic cross-sectional view through the flow cell portion of a liquid chromatography system according to this invention;

FIG. 2 is a fragmentary sectional view showing a first alternative embodiment of that portion of FIG. 1 enclosed within line 2,3—2,3;

FIG. 3 is a fragmentary sectional view showing a second alternative embodiment of that portion of FIG. 1 enclosed within line 2,3—2,3; and FIG. 4 is a graph wherein curve I represents a chromatogram obtained using a conventional unpacked flow cell generally in accordance with prior art procedures, and curve II represents a chromatogram obtained under conditions generally similar to those used in connection with curve I but using a packed flow cell in accordance with this invention.

DESCRIPTION OF PREFERRED EMBODIMENT

FIG. 1 shows a longitudinal cross-sectional view, schematic in nature, through the flow cell assembly portion of a liquid chromatography system operable in accordance with the principles of the present invention.

The preferred flow cell assembly 10 comprises a quartz flow cell 12 of tubular configuration disposed within a housing structure comprising upper and lower parts 26 and 28, respectively. The quartz walls of the flow cell 12 are relatively transparent to a beam of electromagnetic radiation indicated schematically at 14, which is incident upon the flow cell 12 via an aperture 29 through the flow cell housing structure. The aperture 29 is typically a transverse bore through the flow cell housing structure, with the upper part 26 of the housing structure being above the bore and the lower part 28 of the housing structure being below the bore. The mode of detection used is based upon the measurement of fluorescent emissions from chemical species that are present in the mobile phase that passes through the flow cell 12. A conventional fluorescence detector may be used for the purpose.

Typically, the incident radiation 14 is at ultraviolet or visible wavelengths, and is directed from a light source via an appropriate filter through one wall of the cell 12 into the interior thereof, and thence outward through an opposing wall of the cell 12. Although not indicated in the drawing, the detection of fluorescence emitted from fluorescing sample species within the flow cell 12 is preferably accomplished through an aperture located in the flow cell housing structure at 90° with respect to the incident exciting radiation. By viewing the fluorescing radiation at an angle perpendicular to the direction of incidence of the exciting radiation, the fluorimeter detector is least likely to be affected by scattered exciting radiation. Hence, for the embodiment shown in the drawing, fluorescence detection may be most advantageously effected in a direction normal to the plane of FIG. 1. Detection per se is effected in a conventional manner, e.g., by use of a photomultiplier and associated electronic circuitry, as is known in the art.

The quartz flow cell 12 is maintained in position within its housing structure by a pair of Teflon end caps 16 and 18 secured about the inlet and outlet ends, respectively, of the flow cell 12. Central restricted flow channels 20 and 22 are provided through the end caps 16 and 18, respectively. These channels 20 and 22 communicate with the central interior volume 24 of the flow cell 12. The end caps 16 and 18 are retained within central bores of the upper and lower parts 26 and 28, respectively, of the flow cell housing structure. Unions 30 and 32, which are threadingly received into the outwardly facing ends of the upper and lower parts 26 and 28, respectively, serve to couple the flow cell assembly 10 to the flow line of the chromatography system. An inlet line 38 from the chromatographic column is received within the union 30 at the inlet end of the assembly 10, and effluent outlet line 48 is received within the union 32 at the outlet end of the assembly 10. The outlet line 48 may proceed to a waste collector, or to other types of detector apparatuses arranged in series with the fluorescence detector.

For particular applications, it may be advantageous to fashion the flow cell housing structure from two separate pieces corresponding to the upper and lower parts 26 and 28 of FIG. 1. In such a design, the two separate pieces would be maintained in position as by bolts to hold the flow cell 12 in proper relationship with respect to a source of incident radiation and a detector of fluorescence emissions, according to the technique described in connection with FIG. 1.

In the preferred embodiment shown in FIG. 1, the inlet union 30 bears against the Teflon end cap 16. A restricted flow channel 40 in the inlet union 30 provides liquid communication from the inlet line 38 via the restricted flow channel 20 in the end cap 16 to the interior of the flow cell 12. The Teflon cap 16 is compressed to provide a high-pressure seal between the union 30 and the upper end of the quartz flow cell 12. Similarly, the Teflon cap 18 is compressed to provide a high-pressure seal between the union 32 and the lower end of the flow cell 12.

The outlet union 32 is configured to present an annular rim portion in contact with the Teflon end cap 18. The recessed portion of the outlet union 32 defined by the annular rim holds a porous metal plug 36. Liquid communication from the interior of the flow cell 12 is provided through the restricted flow channel 22 in the end cap 18, via the pores in the plug 36, to the restricted flow channel 42 in the union 32 and thence to the effluent outlet line 48. The plug 36 may comprise, e.g., a sintered steel frit of 0.5-micron particle size. The plug 36 serves to close the flow cell volume, which includes the central interior volume 24 and the volume of the channel 22 in the end cap 18.

The plug 36 provides an expedient way to pack the interior volume 24 of the flow cell 12 with a particulate material 46 that is adsorptive of the sample components in the mobile phase, which are to be detected and/or measured. The pores in the plug 36 admit the mobile phase liquid into the flow channel 42, but are small enough to prevent the packing material 46 from passing out of the interior volume 24 of the flow cell 12. The flow cell 12 can be packed with, e.g., silica particles by injecting a slurry of such particles into the cell inlet 38. The porous plug 36 at the cell outlet permits the solvent to pass out from the cell 12, but retains the silica particles. This procedure for packing the flow cell 12 is the same as the procedure commonly used for packing chromatographic columns.

For many applications, it is advantageous to pack not only the interior volume 24 of the flow cell 12, but also the flow channel 20 through the end plug 16 and the flow channel 40 through the union 30, with the sample adsorptive packing material 46 in order to minimize the "dead space" in the flow path of the mobile phase. Peak spreading in the separation of the various sample components can be minimized by making the "dead space" in the flow path between the chromatographic column and the flow cell as small as possible. In effect, it is advantageous for the flow cell to be merely an extension of the chromatographic column so as to optimize component resolution and minimize peak volumes. Smaller peak volumes indicate higher sample concentrations, thereby reducing the minimum quantity of sample species that can be detected.

In an alternative embodiment of a flow cell assembly according to this invention, as shown in FIG. 2, a porous metal plug 34 is fitted within a recessed portion of the inlet union 30'. This plug 34 may be substantially identical to the plug 36 in size and composition. The packing of such a flow cell according to this alternative embodiment with the particulate material 46 may be accomplished by the same technique as described above in connection with the embodiment shown in FIG. 1, using an inlet union that does not have a filter plug 34 installed. Subsequent to the packing operation, a union 30' fitted with the filter plug 34 is substituted for the inlet union that does not have a filter plug installed. Use of such a plug at both ends of the flow path through the flow cell 12 permits the inlet line 38 and the outlet line 48 to be interchanged, without danger of forcing the packing material 46 from the flow cell 12.

In another alternative embodiment of a flow cell assembly according to this invention, as shown in FIG. 3, the porous plug 36 at the outlet end of the flow cell 12, and/or the porous plug 34 at the inlet end of the flow cell 12, are replaced by thin filter plugs (illustrated by the inlet-end filter plug 35 in FIG. 3), which are pressed into the Teflon end caps at the interfaces between the end caps and the corresponding union fittings. The inlet line 38 and the outlet line 48 are preferably fabricated from a smooth, chemically resistant material such as stainless steel.

The operation occurring at the chromatographic column may be normal liquid-liquid chromatography (LLC), bonded-phase chromatography (BPC), or liquid-solid chromatography (LSC). In each of these techniques, a nonpolar mobile phase and a polar stationary phase are customarily used. Thus, in accordance with the principles of the present invention, the liquid mobile phase proceeding from the chromatographic column via the inlet line 38 may be substantially nonpolar. Typical stationary phase components may include water, glycols, beta, betaoxydipropionitrile, and similar polar liquids, and various bonded phase materials, as are known in the art. Typical mobile phase components may include nonpolar solvents such as hexane, heptane, octane, isooctane, benzene, and tetrahydrofuran (THF). For purposes of illustrating this invention, a nonpolar mobile phase may be considered for use even for a liquid-solid chromatography (LSC) process.

In accordance with the invention, the flow cell 12 is packed with the particulate material 46, which is adsorptive of the eluting species to be detected. A preferred packing material comprises a very fine silica gel of the type commonly referred to as "microparticulate silica," i.e., a gel wherein the average particle size is in the range of 5 to 10 microns. A particular packing material that is especially suitable for the practice of this invention is LiChrosorb SI 60, which is marketed by E. Merck Laboratories. Another kind of particulate material suitable for the practice of this invention consists of very finely divided alumina particles, i.e., a particulate of alumina wherein the average size of the particles is in the range of 5 to 10 microns. A material of this kind is marketed by E. Merck Laboratories under the product designation Alox T.

Chemically bonded phase particles may also be used for packing the flow cell 12 in accordance with this invention. The term "bonded phase particles," as understood by those familiar with the chromatographic art, refers to those particulates that are customarily used in the packing of chromatographic columns for "bonded phase chromatography." Bonded phase chromatography (BPC) is a technique wherein a stationary support material such as silica is chemically reacted so that the stationary phase, which may be a liquid or a solid, is bonded thereto. The "bonded" stationary phase thereupon interacts with the flowing mobile phase in the chromatographic process. A detailed discussion of bonded phase particles for use in BPC can be found, e.g., at pages 4–14 through 4–16 of the reference work entitled *Basic Liquid Chromatography* by Nina Hadden et al., published in 1971 by Varian Associates, the assignee of this patent application.

The curves I and II in FIG. 4 are chromatograms that illustrate the enormous improvement in detection capability that can be achieved with the fluorescence chromatography technique according to the present invention. For both curves I and II, the ordinate units provide a proportionate indication of the intensity of the fluorescent radiation emitted by the sample components in the flow cell as a result of excitation by incident electromagnetic radiation. However, the scale factors for the ordinates are quite different for curves I and II as indicated by the ordinates of FIG. 4. For curve I, the full scale range is 5 millivolts; whereas, for curve II, the full scale range is 200 millivolts. Thus, if curves I and II were drawn to the same ordinate scale, the peaks on curve II would appear 40 times higher with respect to the peaks on curve I than as shown in FIG. 4. The abscissa indicates time in minutes, using the same scale for both curve I and curve II.

The lower curve, curve I, of FIG. 4 is a chromatogram illustrating the detection capability of a chromatographic system utilizing a flow cell as in FIG. 1 without the packing material 46. Although certain construction details of the device shown in FIG. 1 may differ from those of conventional flow cells, e.g., in the use of the porous plug 36, nevertheless the basic mode of operation (without use of the packing material 46) does not differ substantially from that of the prior art for using fluorimeters in liquid chromatography systems.

The data illustrated in curve I were derived from a normal phase separation using a conventional bonded phase CN column (i.e., a column wherein the stationary phase comprises a cyano- functional group bonded to the surface of silica support particles) for the chromatographic separation and fluorimetric detection of certain aflatoxins, viz, aflatoxins B1, B2 G1 and G2, which are toxic metabolites of fungus that under certain conditions can grow on plants such as peanuts and cereals. A pair of non-polar solvent A and B were used in an isocratic mode of operation. More specifically, the A solvent was hexane; and the B solvent was a mixture of 10% isopropyl alcohol, with 1% water, and 89% tetrahydrofuran (THF). The ratio of solvent A to solvent B was 70 to 30 by volume. The flow rate of the mobile phase was 1 milliliter per minute. The excitation source provided a wavelength of 360 nanometers utilizing appropriate color-glass filters, such as the filters marketed by Corning Glass Works Inc. under the designation numbers C.S. 7-60 and C.S. 7-54, with emission being measured at the 430-nanometer wavelength through an appropriate interference filter. With the unpacked cell, the background reading was approximately 8 millivolts, and the noise level was approximately 0.02 millivolts. The background reading was compensated by a conventional zero-offset circuit to enable presentation of detection signals on a 5-millivolt full scale deflection range.

Curve II is a chromatogram illustrating the detection capability of a chromatographic system utilizing a flow cell as in FIG. 1 that is packed according to this invention. The data illustrated in curve II were derived using identical sample components and following the same analysis techniques as were used to derive the data for curve I. As previously mentioned, the ordinate scale for curve II is greater than the ordinate scale for curve I by a factor of 40, i.e., full scale deflection for curve II corresponds to 200 millivolts. The high degree of scattering caused by the packing material in the flow cell is responsible for a high background signal of 450 millivolts, and a noise level of 0.26 millivolts. The background reading for curve II was compensated by a conventional zero-offset circuit to enable presentation of detection signals on a 200-millivolt full scale deflection range.

Both the chromatograms, curves I and II, were obtained for injections of 2.0 nanograms of B1 aflatoxin, 0.6 nanograms of B2 aflatoxin, 2.0 nanograms of G1 aflatoxin, and 0.6 nanograms of G2 aflatoxin.

In Table I hereinbelow, data are listed for the respective experimental runs illustrated by curves I and II. The detection signal levels and the corresponding minimum detectable quantities (MDQ's) achieved with the packed flow cell of this invention are compared with corresponding data for an unpacked flow cell for the various aflatoxins. This comparison establishes that the packed flow cell of this invention provides minimum detectable quantities of aflatoxins B1 and B2 that are more than 100 times smaller than the corresponding minimum detectable quantities for the same aflatoxins using the unpacked flow cell of the prior art.

Cross reference should be made to the correspondingly identified peaks on curves I and II, whereby a four-fold improvement in the sensitivity and detection of G1 and G2 aflatoxin for curve II becomes apparent. From this comparison, it is evident that the stationary phase packing material 46 in flow cell 12 has an effect on quantum yield similar to the effect of a polar mobile phase. Thus using this flow cell packing technique the chromatographic operation can be optimized while using the most advantageous solvents, which need not be strongly polar.

TABLE I

| Afla-toxin | Packed Cell | | Unpacked Cell | |
|---|---|---|---|---|
| | Signal (mv) | MDQ (pq) | Signal (mv) | MDQ (pq) |
| B1 | 138 | 8 | — | 1000 |
| B2 | 84 | 4 | — | 1000 |
| G1 | 88 | 11 | 1.9 | 42 |
| G2 | 62 | 5 | 0.9 | 26 |

The present invention has been particularly set forth above in terms of specific embodiments. It is to be understood that variations upon the invention are now enabled to those skilled in the art by reason of this disclosure, which variations lie within the scope of the present teaching. Accordingly, this invention is to be broadly construed, and is limited only by the scope and spirit of the following claims.

What is claimed is:

1. A method for enhancing the fluorescent detectability of an aflatoxin present in a solvent, said method comprising the step of passing an aflatoxin-bearing eluant from a liquid chromatography column through a flow cell packed with aflatoxin-adsorbing particles, whereby there is caused a dynamic equilibrium of the aflatoxin between the solvent of the eluant and said particles, and whereby said detectability is enhanced; said flow cell having a wall portion that is substantially transparent to electromagnetic radiation of a frequency that causes the aflatoxin to fluoresce.

2. The method of claim 1 wherein said solvent of the eluant comprises a nonpolar liquid.

3. The method of claim 1 wherein said particles comprise microparticulate silica.

4. The method of claim 1 wherein said particles comprise alumina.

5. The method of claim 1 wherein said particles comprise a bonded phase particulate material.

6. The method of claim 1 wherein said particles comprise an ion-exchange resin.

7. A chromatographic method for detecting the presence of an aflatoxin in a sample material, said method comprising in sequence the steps of:
 (a) passing said sample material through a liquid chromatography column;
 (b) passing the outflow of said column through a flow cell packed with aflatoxin-adsorbing particles whereby there is caused a dynamic equilibrium of the aflatoxin between the mobile phase and said particles;
 (c) irradiating said flow cell with electromagnetic radiation of a frequency that causes the aflatoxin to fluoresce; and
 (d) detecting the emitted fluorescence.

8. The method of claim 7 wherein said outflow includes at least one nonpolar solvent.

9. The method of claim 7 wherein said particles comprise microparticulate silica.

10. The method of claim 7 wherein said particles comprise alumina.

11. The method of claim 7 wherein said particles comprise a bonded phase particulate material.

12. The method of claim 7 wherein said particles comprise an ion-exchange resin.

13. The method of claim 7 wherein said radiation is incident upon said flow cell at approximately right angles to the direction of fluorescence detection.

14. The method of claim 7 wherein said flow cell of packed with said particles by closing the outlet of said cell with a porous metal plug, injecting a slurry containing said particles into the inlet of said cell, and withdrawing the liquid phase of said slurry from said cell outlet through said plug.

15. The method of claim 7 wherein a fluorimeter detector is used in detecting said emitted fluorescence.

16. A fluorescence spectrometer comprising:

(a) a flow cell through which an aflatoxin present in a solvent and having been eluted from a liquid chromatography column can pass, said flow cell being packed with aflatoxin-adsorbing particles whereby there is caused a dynamic equilibrium of the aflatoxin between the solvent and said particles;

(b) means for irradiating the aflatoxin with electromagnetic radiation of a frequency that causes the aflatoxin to fluoresce; and (c) means for detecting the emitted fluorescence;

said flow cell having a wall portion that is substantially transparent to said electromagnetic radiation.

17. The spectrometer of claim 16 wherein said solvent comprises a nonpolar liquid.

18. The spectrometer of claim 16 wherein said particles comprise microparticulate silica.

19. The spectrometer of claim 16 wherein said particles comprise alumina.

20. The spectrometer of claim 16 wherein said particles comprise a bonded phase particulate material.

21. The spectrometer of claim 16 wherein said particles comprise an ion-exchange resin.

* * * * *